(12) United States Patent
Mosqueira et al.

(10) Patent No.: US 10,098,840 B2
(45) Date of Patent: Oct. 16, 2018

(54) NANOPARTICULATE COMPOSITION CONTAINING ANTIBIOTICS FOR INTRAMAMMARY ADMINISTRATION IN ANIMALS

(75) Inventors: Vanessa Carla Furtado Mosqueira, Ouro Preto MG (BR); Raquel Silva Araújo, Ouro Preto MG (BR); Humberto de Mello Brandão, Juiz de Fora MG (BR)

(73) Assignees: UNIVERSIDADE FEDERAL DE OURO PRETO, Ouro Preto MG (BR); EMPRESA BRASILEIRA DE PESQUISA AGROPECUARIA-EMBRAPA, Juiz de Fora MG (BR); FUNDAÇÃO DE AMPARO À PESQUISA DO ESTADO DE MINAS GERAIS-FAPEMIG, Belo Horizonte MG (BR)

( * ) Notice: Subject to any disclaimer, the term of this patent is extended or adjusted under 35 U.S.C. 154(b) by 0 days.

(21) Appl. No.: 13/700,963

(22) PCT Filed: Jun. 1, 2011

(86) PCT No.: PCT/BR2011/000168
§ 371 (c)(1),
(2), (4) Date: Mar. 4, 2013

(87) PCT Pub. No.: WO2011/150481
PCT Pub. Date: Dec. 8, 2011

(65) Prior Publication Data
US 2013/0189368 A1   Jul. 25, 2013

(30) Foreign Application Priority Data
Jun. 1, 2010   (BR) .................... 1002601

(51) Int. Cl.
| | | |
|---|---|---|
| *A61K 9/10* | (2006.01) | |
| *A61K 9/00* | (2006.01) | |
| *A61K 9/51* | (2006.01) | |
| *A61K 31/431* | (2006.01) | |
| *A61K 9/19* | (2006.01) | |
| *A61K 45/06* | (2006.01) | |
| *A61K 31/43* | (2006.01) | |
| *A61K 31/545* | (2006.01) | |

(52) U.S. Cl.
CPC .............. *A61K 9/10* (2013.01); *A61K 9/0041* (2013.01); *A61K 9/19* (2013.01); *A61K 9/5161* (2013.01); *A61K 31/43* (2013.01); *A61K 31/431* (2013.01); *A61K 31/545* (2013.01); *A61K 45/06* (2013.01); *Y02A 50/491* (2018.01); *Y02A 50/492* (2018.01)

(58) Field of Classification Search
CPC ...... A61K 31/431; A61K 9/0041; A61K 9/10; A61K 9/19; A61K 9/5161
See application file for complete search history.

(56) References Cited

U.S. PATENT DOCUMENTS 5,843,509 A * 12/1998 Calvo Salve ............ A61K 9/10
                                                424/489
2009/0074824 A1 * 3/2009 Vila Pena ................ A61K 8/11
                                                514/1.1

FOREIGN PATENT DOCUMENTS

WO    WO 9939700 A1 * 8/1999 ........... A61K 9/5123

OTHER PUBLICATIONS

Vauthier, C.; Bouchemal, K. "Methods for the Preparation and Manufacture of Polymeric Nanoparticles" Pharmaceutical Research, vol. 26, No. 5, May 2009.*
Pubchem. (https://pubchem.ncbi.nlm.nih.gov/compound/amoxicillin) accessed Mar. 11, 2016, p. 1-49.*

* cited by examiner

Primary Examiner — Andrew S Rosenthal
(74) Attorney, Agent, or Firm — Sughrue Mion, PLLC (57) ABSTRACT

The present invention relates to the development of two types of polymer nanocapsules to encapsulate cloxacillin benzathine, an antimicrobial drug. More specifically, this invention relates to a new form of treatment for mastitis in dairy cattle. Two nanocapsule formulations have been developed and can be used to encapsulate various drugs, besides cloxacillin benzathine, providing a new therapy for mastitis in cows, avoiding the inconvenience of the use of high doses of drugs used in conventional formulations, thus contributing to an improvement in milk quality.

19 Claims, 2 Drawing Sheets

NANOPARTICULATE COMPOSITION CONTAINING ANTIBIOTICS FOR INTRAMAMMARY ADMINISTRATION IN ANIMALS

The present invention relates to the development of two formulations of polymer nanocarriers (NC) which encapsulate antimicrobial drugs derivatives of penicillin, such as cloxacillin benzathine. More specifically, this invention relates to a new composition for the treatment of mastitis in livestock (cattle, goats, sheep, buffaloes, horses and camelids) in the dry period.

DESCRIPTION OF THE INVENTION

The present invention describes a technique of preparing two nanocarrier formulations of the reservoir type that can encapsulate various drugs with antibiotic activity, particularly the drug benzathine cloxacillin, widely used in the treatment of bovine mastitis. The present invention aims at providing a new therapy for mastitis in dairy cattle, avoiding the inconvenience of administering repeated doses, the use of high doses of drugs used in conventional formulations, the low retention of the drug inside the teat, contributing to an improvement in milk production. By using this formulation the efficacy of the drug can be increased due to the high adhesion of the nanocarriers mentioned herein to the glandular tissues of the upper portions of the udder of the animals. In addition, the drug in its free form, as it is used in commercial formulations, is available to reach the blood from the site of administration, and therefore can reach other tissues other than those affected by microorganisms that cause mastitis. The drug in the nanoencapsulated form is more restricted to the sites of action in the tissue and in the target cells of infection by agents that cause microbial mastitis, due to the specificities of the components of the formulation and the method of production of the nanostructured formulations presented herein. The encapsulated antimicrobial drug can thus achieve specific target and be released slowly and mainly in the site of action, avoiding loss or inactivation of the drug in other tissues. Thus the doses can be reduced and the efficiency increased.

Bovine mastitis remains a limiting factor in milk production in many properties in Brazil, emerging as the most frequent cause of profit loss to milk producers. Treatment is limited to clinical emergency cases when the loss is already inevitable. Antibiotics and anti-inflammatory are the most commonly used drugs for the treatment of mastitis (Gruet et al., 2001).

Mastitis in dairy cattle frequently occurs during the dry period or in early lactation. The main bacteria causing mastitis, *Staphylococcus aureus*, can form encapsulated focuses in upper portions of the udder, developing a sub-clinical form, which hinders the bacteriological cure during lactation, because antibiotics used in this phase are short-shot (i.e. short half-life in the target of action), due to the milking period, not remaining at therapeutic levels for long enough to determine the complete elimination of bacteria in cystic form. In this case, if there is no treatment during drying, these bacteria can resist the whole dry period and return in the next lactation. Other bacteria have been isolated during the dry period, such as *Streptococcus uberis*, *Streptococcus agalactiae*, and *Corynebacterium pyo* genes, which are also among the agents causing microbial mastitis. The treatment of the animals during the dry period reduces both the number of infections during this phase as the number of new infections in the beginning of lactation. In average, it is possible to eliminate 90% of the infections caused by *Streptococcus agalactiae* and 70% by *Staphylococcus aureus* with the treatment in the dry period (Naztke, 1971). However, the efficacy can be increased if the retention of the drugs in the infection sites is also increased.

The majority of the formulations commercialized in Brazil for the treatment of mastitis in bovine is of the intramammary-suspension type, as in the case of Orbenin® Extra Dry Cow. There are also antibiotic associations, as in the case of Bovamast® (Bayer), which is a suspension of antibiotics benzathine cloxacillin and ampicillin. Several treatments are available, among which are those that prevent the disease and those that treat it. Therefore, compositions for cleaning the teats are presented in the U.S. Pat. No. 5,211,961, where it is used as an antimicrobial douche.

Another alternative, present in EP 1104233 and EP 799047 relate to compositions capable of forming a film which can be applied to the teats of the animals to form a barrier to bacteria. Another form involves forming a physical barrier in the teat canal to prevent the entrance of pathogens as described in GB 1441747. GB 2273443 describes the use of an antibacterial formulation and a barrier to treat mastitis in cows. For example, in GB 2273441 this barrier is formed by a gel and a non-toxic heavy metal salt. Contrary to the expected, the co-administration of an oil-based product with a formulation that blocks the teat canal containing a heavy metal salt leads to improvement in the barrier effectiveness as disclosed in GB 2296424. Several types of oils are used, such as mineral, silicone and vegetable oils. However, there is the risk of the accumulation of heavy metals in the organism of the animal and subsequent contamination of milk during lactation.

Most of the formulations cited above have the disadvantage of not eliminating the focus of cystic bacteria, which leads to recurrence of infection in animals. The formulations which act as a barrier (GB 1441747, GB 2296424) have a preventive character and are not effective in already infected animals.

The products commercialized in Brazil for the treatment of bovine mastitis have the drawback of using high doses of drug (usually 500-600 mg per teat) by intramammary route. These treatments have the drawback of multiple infusions (1 to 4 applications during the dry phase) which may cause sores in the teat canal of the animal due to the canula whereby the suspension penetrates into the udder, increasing the risk of contamination of the gland with new pathogens during administration.

The traditional formulations used do not allow the drug to internalize into target cells. The free drug, more soluble, has little chance of penetration in high concentrations in infected neutrophils, not eliminating focuses of intracellular infection, generating post-treatment late relapse. The proposed formulation, due to its constitution, has the capacity of adhesion and intracellular penetration in the mammary gland cells (phagocytes and acini surface cells, duct and gland cisterns) penetrating by phagocytosis, nonspecific endocytosis and physical adsorption in the cell surface (Mosqueira et al. 1999), both by electrostatic interactions of nanocarriers with the cell membrane and by hydrophobic interactions with proteins and glycoproteins. These formulations have a great differential due to their increased capacity of residence and adhesion inside the gland, which increases the chances of resolution of infection (efficacy) and potentially reduces relapses, mainly because the mammary gland has a high concentration of neutrophils (Oliveira et al., 2009). Recurrences are frequent with traditional formulations which do not have high intracellular penetration and thus do not reach the minimum inhibitory concentration (MIC) within the intracellular compartment. The free drug penetrates into the cells by other slower and transport-dependent unimolecular mechanisms, whereas in the nanoparticulate form a much larger number of molecules penetrate at once into the cells, encapsulated inside the nanocarriers, acting as a "Trojan Horse". Another form is the non-specific adhesion of thousands of nanocapsules on the surface of cells, which promotes the absorption of a larger amount of drug by the target cell.

The nanoencapsulation also prevents the rapid metabolism of the drug by the cells after administration and prevents the rapid elimination of the drug from the site of action, which occurs when the drug is administered in its free or non-encapsulated form. The excipients used in the proposed formulations are innocuous, biodegradable, biocompatible, of natural origin and do not compromise the functions of the gland, not producing any type of cell damage or cytotoxicity (Mosqueira et al., 2000 and 2001).

In this context, the administration of a nanoparticulate formulation by intramammary route is a promising alternative for the effective treatment of mastitis in dairy cattle. Its application has the potential to increase drug retention in cells infected with microorganisms, especially by *S. aureus*. An important property of the formulations of the present invention is the ability to remain at the site of action during the dry period of the animal (transition period between two lactations).

Such nanostructures can encapsulate drugs such as antibacterial, antifungal, antiparasitic, vitamins, nonsteroidal anti-inflammatory, steroidal anti-inflammatory, antiviral, antineoplastic, anesthetic, hormones or combinations thereof and be administered by different routes of administration such as oral, intra-articular, parenteral, ocular, mammary, topical, nasal, otologic, rectal, vaginal and/or a combination of these routes.

The present invention aims at providing a new therapy for the treatment and prophylaxis of diseases in non-human animals bypassing the inconvenience of administration of multiple doses and the use of high doses of drug used in traditional formulations, which reduces animal stress and the occurrence of residues (of the drug) in the animal products. The nanoparticulate compositions of drugs for veterinary use also reduces the occurrence of side effects in relation to the use of the drug in free form, because the nanostructures proposed herein direct the drug in the animal body to the desired target of action, reducing the erratic distribution of the free drug. By using these formulations, the drug efficacy can be increased due to the active targeting, to the adhesiveness and the ability of the nanocarriers to accumulate in tissue in which an increase in vascular permeability occurs (passive targeting). These can be the tissues in which the nanoparticles accumulate, for example, inflamed, and neoplastic tissues, besides organs with intense phagocytic activity such as the spleen, liver, lymph nodes, lung, bone marrow and mucous membranes in general. Moreover, the drugs in their free form as they are administered in commercial formulations require multiple administrations in order to achieve high concentrations in different tissues, causing variations in plasma levels that are causing toxicity and/or development of microbial resistance. Drugs in nanoencapsulated form show extended release and are more restricted to sites of action and target cells, due to the specificities of the components of the formulation and their physico-chemical characteristics. Thus, the encapsulated drugs can achieve the specific target and be released slowly and mainly in the site of action, avoiding loss or inactivation of the drug in other tissues. Thus, doses can be reduced, efficacy can be increase and toxicity can be reduced, reducing the need for containment and excessive manipulation of animals. Containment and change in handling are factors that hinder the proper treatment of animals. These conditions are major causes of stress, resulting in endogenous release of adrenaline, noradrenaline and corticosteroids, which results in increased activity (fight-or-flight response) and decreased immunity. This situation worsens as the administration of the drug needs to be more frequent. Due to these difficulties, drug intervention may fail or be late. Additionally, the need for multiple administrations to maintain therapeutic concentration can lead to transposition of the toxicity threshold of the drug, causing adverse effects and an increase in drug residues in animal products (Vandamme, 2010).

According to França-Filho et al. (2006), among the major economic losses associated with beef cattle is the stress caused by handling, which can lead to losses of up to one kg weight/handling and abscess formation due to the application of veterinary drugs using oily vehicle. However, the use of controlled delivery systems in veterinary medicine may reduce the frequency of administration of the drug, reduced duration of treatment and reduced stress for the animals (Sautter, 2006).

Particularly, the present invention allows the delivery of hydrophobic and amphiphilic drugs in nanodispersed form in aqueous vehicles. Therefore, this invention makes possible the administration of water-insoluble drugs by a number of routes of administration including intravenous route.

Most commercial formulations on the market have short half-life drugs and, to reduce the number of applications, industry uses poorly soluble salts thereof in aqueous and oily vehicles, as in the case of Terramycin®. A second strategy is to increase the concentration of the active principle in the formula, as in the case of Ivomec® Gold, which has a concentration of ivermectin 3.15 fold higher when compared to simple Ivomec®. In both cases there are limitations. In the first, tissue necrosis can occur due to incorrect application, as well as the limitation of volume to be applied in the same location, in addition to the possibility that the location wherein the drug is administered may become extremely painful. In the second case the increase in drug concentration may result in toxicity in more sensitive individuals. In turn, the nanocarriers of the present invention are able to vectorize poorly soluble salts in aqueous vehicle while maintaining a sustained and often controlled release. Such condition further allows its intravenous application and, by using an aqueous vehicle, minimizes post-application pain when compared to the oily vehicle.

Another strategy used to overcome the need for multiple applications of drugs is the use of inserts and implants. Baeyens et al. (2000) describes the uses of inserts for the treatment of eye infections in animals; however, such devices cause great discomfort to the patient, in addition to the need for microsurgery and the risk of infection. The nanocarriers described in the claims of the present document are not noticed by the animal because they have nanometric size, and also have the advantage of remaining adhered to the eye mucosa due to the mucoadhesive characteristic conferred by the chitosan (Ilium et al., 2001) coating the nanocarrier. The mucoadhesive characteristic of said nanocarriers also allows them to be used through other routes of administration, where the existence of mucosa gives support to adhesion, namely, oral, nasal, anal and vaginal routes. In turn, Rathbone et al. (2000) report the use of intravaginal and subcutaneous devices for the controlled release of hormones, aiming at controlling the estrous cycle of animals. However, such devices require at least two containments of the animals and, depending on the type/location of implant a more invasive intervention is necessary, which can be surgical. In order to promote the controlled release of drugs without requiring the removal of the implant, document U.S. Pat. No. 4,938,763 discloses the use of biodegradable implants for the controlled release of cisplatin; however, they require a more invasive action when compared to the present invention, wherein administration can be made with the aid of needle and syringe.

Even though there are numerous articles in literature that mention the use of polymeric nanoparticles for controlled release or targeting of drugs for veterinary use, none of them defined which group of drugs can be encapsulated, which route of administration of the drug must be used, or which disease can be treated with such nanostructures (Rather et al. "Nanotechnology: A Novel Tool for Aquaculture and Fisheries Development".

Fisheries and Aquaculture Journal, Volume 2011: FAJ-16; Ramirez-Mella and Hernández-Mendo "Nanotechnology on Animal Production", Tropical and Subtropical Agroecosystems, 12 (2010): 423-429; Chakravarthi and Balaji "Applications of Nanotechnology in Veterinary Medicine" Veterinary World, 2010, v. 3 (10): 477-480; Narducci, "An Introduction to Nanotechnologies: What's in it for Us?" Veterinary Research Communications, 31(Suppl. 1) (2007) 131-137; Scott "Nanotechnology and animal health" Rev. sci. tech. Off. int. Epiz., 2005, 24 (1), 425-432). In the Article, "Low-energy nanoemulsification to design veterinary controlled drug delivery devices" Vandamne and Anton (International Journal of Nanomedicine, 2010:5 867-873) describe the production of nanoemulsions for treating cattle, swine and poultry, in which ketoprofen, sulfamethazine and vitamin D are encapsulated; however, they do not describe which diseases can be treated. When comparing the nanoemulsion produced by Anton and Vandamme to the nanoreservoirs of the present invention, the latter are more stable in physiological media rich in proteins, basically due to the presence of rigid polymeric coating. Additionally, the nanoemulsions described are incapable of targeting the active principle.

On the market, the nanostructured products Paccal® Vet (paclitaxel), Doxophos® Vet (doxorubicin), Carbomexx® Vet (carboplatin), Docecal® Vet (docetaxel), based on the Oasmia's platform of production of nanometric micelles from XR-17, an acrylic ester with hydroxyl functional group, are available for purchase. The production company reports the reduction of toxicity of chemotherapeutic drugs used in the formulation when applied to dogs and cats, but does not report targeting or bioadhesion characteristics of the system. In addition, micellar systems have limited stability in biological medium due to the lack of a hard polymer coating and to the destruction of its structure after dilution in water. As described in U.S. Pat. No. 7,850,990 liposomes can also be used to promote controlled release and targeting of anticarcinogenic chemotherapeutics and others veterinary drugs; however, they present the same stability limitations in a biological environment as micellar systems and present high cost and difficulties in physico-chemical stabilization.

In patent document US 20100150832, the authors describe the preparation of nanoparticles capable of promoting the controlled release and targeting of drugs, using polyketal polymers. However, these nanoparticles do not have mucoadhesive ability as those presented herein, they are readily hydrolyzable in water, and the document does not describe the possible infections to be treated with the proposed system. Patent document U.S. Pat. No. 7,767,656 describes the preparation of nanoparticles from blends of methylcellulose polymers and hyaluronic acid. Due to the hydrophilicity of these polymers, these systems are less efficient in encapsulating hydrophobic agents when compared to the present invention. Additionally, there is no mention in said document of the surface electric charge of the nanoparticle, a factor that is relevant to the targeting and mucoadhesion of the same due to electrostatic interaction.

The mechanism of incorporation of drugs into nanopores and their subsequent application as controlled release system has been proposed in U.S. Pat. No. 7,713,573; however, the high polydispersity of nanopores prevents its use by intravenous route. Moreover, the need for elevating temperature and pressure to incorporate drugs to the nanopore is restrictive for various therapeutic compounds.

Document U.S. Pat. No. 7,585,521 proposes the use of ceramic nanoparticles for controlled release of drugs, including veterinary drugs. Differently from the nanoparticles of the present invention such particles are not biodegradable and some of the substances forming their composition, such as silica nanoparticles, are responsible for silicosis in animals.

Additionally, none of the patent documents (i.e. U.S. Pat. No. 7,585,521; U.S. Pat. No. 7,713,573; U.S. Pat. No. 7,767,656; U.S. Pat. No. 7,767,656; U.S. Pat. No. 7,767,656; US 20100150832; U.S. Pat. No. 7,850,990) define the diseases to be treated in non-human animals, which occurs in the present invention.

In this context, the application of nanoparticulate formulations containing antibacterial, antifungal, antiparasitic, vitamins, nonsteroidal anti-inflammatory, steroidal anti-inflammatory, antiviral, antineoplastic, anesthetic and/or hormones administered by oral, parenteral, ocular, breast, topical, intra-articular, nasal, ear, rectal, vaginal and/or combination of these routes is a promising alternative for the treatment and effective prophylaxis of diseases in non-human animals.

The Nanocarriers containing one or more antibacterial, antifungal, antiparasitic, vitamins, non-steroidal or steroidal anti-inflammatory drugs, antiviral, antineoplastic drugs, anesthetics or hormones as active principle of the present invention are selected from the group of sulfonamides, nitrofuran, quinolones, fluoroquinolones, the cephalosporins of first to fifth generation, aminoglycosides, macrolides, lincosamides, chloramphenicol, tetracyclines, polymyxins, beta-lactam, systemic antimycotics, topic antimycotics, liposoluble vitamins, neuraminidase inhibitors, reverse transcriptase inhibitors, non-glycoside inhibitors of reverse transcriptase, protease inhibitors, nucleoside analog reverse transcriptase inhibitors, benzimidazoles, imidathiazoles, tetrahydropyrimidines, organophosphates, avermectins, milbemycin, heterocyclic compounds, arsenicals, nitroscanate, benzimidazoles, rafoxanide, imidines, imidothiazoles, niclosamides, carbamates, pyrethroids, imidacloprids, antiprotozoal, salicylanides, imidacloprids, corticosteroids, antiinflammatory non steroidal drugs, salicylates, anthranilic acid derivatives, benzydamines, arylalkanoic derivatives, propionic acid derivatives, pyrazolone derivatives, ergot alkaloids, protein hormones, gonadotropin-releasing hormone analogue, agents for alkylating steroid hormone, antimetabolite agents, natural or synthetic antineoplastic, and/or their combination with other actives; examples of active principles are sulfamethazine, sulfamerazine, sulphaquinoxaline, sulfachloropyridazine, sulfadiazine, sulfanilamide, sulfathiazole, sulfisoxazole, sulfamethizole, sulfacetamide, sulfamethoxazole, sulfaphenazole, sulfamoxole, sulfamethoxine, sulfametonidine, sulfadoxine, sulfamethoxypyrazine, sulfadimethoxine, sulfaguanidine, phthalylsulfathiazole, succinylsulfathiazole, phtalylsulfacetamide, nitrosulfathiazole, sulfacetamide, mafenide, sulfadiazine and salts thereof, sulfachloropyridazine, sulfadimerazine, sulfadimidine, sulfaethoxypyridazine, sulfafurazole, sulfameter, sulfa methylpyridine, sulfameth, sulfametopyrazine, sulfamethoxydiazine, sulfamethoxydine, sulfamethoxypyridazin, sulfamethoxypyrimidin, sulfamezathine, sulfamidine, sulfamido dimethylpyrimidine, sulfamonomethoxine, sulfanylacetamida, sulfanilamidopyrimidine, sulfanilaminothiazole, sulfanilguanidine, sulfapyridine, sulfapyrimidine, sulfasalazine, sulfathalidine, furaltadone nitrofurantoin, furazolidone, furoxone, nitrofurazone, dapsone, nalidixic acid, oxolinic acid, pipemidic acid, ciprofloxacin, enrofloxacin, lomefloxacin, norfloxacin, ofloxacin, perfloxacin, rosoxacin, levofloxacin, acrosoxacin, cinoxacin, besifloxacin, penicillin, netacilina, tameticilina, doxycycline, benzilpenicilinas (penicillin V, phenoxymethylpenicillin and G sodium, potassium, procaine or benzathine penicillins), aminopenicillins (ampicillin, amoxicillin, hetacillin and carbenicillin), hetacillin, isoxazolylpenicilins (oxacillin, cloxacillin and dicloxacillin) and antipseudomonal penicillin (ticarcillin, piperacillin, azlocillin and meziocilina), ceftiofur, cefadroxil, cephalexin, cephaloridine, cefatotina, cefapirin, cefaloniun, cefazolin, cephradine, cefacetrile, cefaclor, cefamandole, cephamycin, cefonicid, ceforanide, cetoxitin, cefuroxime, cefquinome, cefixime, cefoperazone, cefotaxime, ceftazidime, ceftizoxime, cefoxazole, ceftriaxone, moxalactan, vancomycin, trimethoprim, aminocidine, rifaximin, tiamulin, spectinomycin, aminosidine, streptomycin, dihydrostreptomycin, gentamycin, neomycin, tyrothricin, kanamycin, dibekacin, netilmicin, tobramycin, framycetin clavulanic acid, rifamycin, fusidic acid, oleandomycin, penethamate amikacin, bacitracin, clindamycin, erythromycin, spiramycin, lincomycin, novobiocin, pirlimycin, tylosin, chlortetracycline, doxycycline, minocycline, oxytetracycline, tetracycline, polymyxin B or polymyxin (colistin), nystatin, griseofulvin, amphotericin b, ketoconazole, itraconazole, terbinafine, tolciclate, tioconazole, clotrimazole, isoconazole, miconazole, ciclopirox olamine, fluconazole, mebendazole, flubendazole, fenbendazole, cambendazole, albendazole, oxibendazole, oxfendazole, parbendazol, thiabendazole, thiophonate, amitraz, tetramisole, levamisole, febantel, niclosamide, praziquantel, pyrantel pamoate, pyrvinium pamoate, morantel tartrate, trichlorfon (metrifonate), diclorves, chlorpyrifos, malathion, diazinon, dimethoate, fenthion, abamectin, ivermectin, moxidectin, doramectin, nemadectin, milbemycin oxime d, phenothiazine, piperazine, nitroxynil, disophenol, thiacetarsamide (arsenamide) melarsomine dihydrochloride, mebendazole, fenbendazole, albendazole, cambendazole, thiabendazole, parbendazole, flubendazole, oxfendazole, triclambendazole, febantel, thiophanate, netobirnin, arsenious oxide, melarsoprol, tetramizole, levamizole, methylcarbamates, parbendazole, mebendazole, flubendazole, flumethrin, permethrin, cypermethrin, deltamethrin, closantel, rafoxanide, tetraetiuran monosulfide (monosulfiram) chloronicotinyl nitroguanidine, fipronil, lufenuron, nitenpyram, metronidazole, pyrimethamine, amprolium, clopidol, monenzin, nicarbazin, toltrazuril, maduramicin, narazin, nitrofurazone, diaminazen aceturate, imidocarb, diquinolilurea, primaquina, hidrocortisona, cortisone, prednisone, prednisolone, methylprednisolone, triamcinolone, paramethasone, betamethasone dexamethasone, flumethasone, dipirone, phenylbutazone, aminopyrine, naproxen, flunixin meglumine, pranoprofen, surofeno, flurbiprofen, sodium diclofenac, acetylsalicylic acid, salicylic acid, paraminofenol, idoxuridine, acyclovir, ganciclovir, amantadine, rimantadine, oseltamivir, zanamivir, nevirapine, delavirdine, efavirenz, zidovudine, didanosine, zalcitabine, stavudine, lamivudine, abacavir, emtricitabine, amprenavir, fosamprenavir, indinavir, ritonavir, saquinavir, nelfinavir, tenofovir, adefovir, vitamin K, vitamin A, vitamin D, vitamin E, tetracaine, proxymetacaine, lidocaine, xylazine, ketamine, ergovine maleate, methylergometrine maleate, bromocriptine, nechlorethamine, cyclophosphamide, melphalan, chlorambucil, ethylenamines (triethylenthiophosphoramide), alkyl sulfonates (busulfan), nitrosureas, triazenes (dacarbazine), folic acid analogs (methotrexate), pyrimidine analogs (fluorouracil, cytarabine), purine analogs (mercaptopurine), cisplatin, 1-asparginase, hydroxyurea, vinblastine, vincristine, doxorubicin, dactinomycin, bleomycin, diethylestilbestrol; estradiol cyprionate, allyltrenbolone, medroxyprogesterone acetate, megestrol acetate, progesterone, cloprostenol sodium, dinoprost tromethamine, altrenogest, fluprostenol, tiaprost, prostaglandin F-2-alpha, melatonine, human chorionic gonadotropin, follicle stimulating hormone, equine chorionic gonadotropin, luteinizing hormone, gestrinone, gonadorelin, goserelin, buserelin, leuprolide, danazol, deslorelin, growth hormone, testosterone propionate, testosterone cypionate or oxytocin, not restricted to these active principles, its derivatives, their salts and/or combinations thereof, highlighting that the active ingredient to be incorporated into the nanosystems may belong to any of the above groups.

Thus, in order to obtain a product for mastitis' treatment, characterized by an intramammary administration, or even by parenteral local injections, which does not need multiple infusions (single dose and extended release) and which has the capability of adhere and penetrate in the infected cells of the mammary gland of the animal (direction of the active principle) it came to the which is the object of this invention, which presents a new formulation of antibiotic encapsulated in nanocarriers of lipidic and polymeric nature.

Despite of the existence in the literature of micro particles containing antibiotics in order to treat the mastitis, for example in the following works from: Ziv and Linder. "Encapsulated forms of slow-release dry cow products of rapidly absorbed antibiotics". Journal of Veterinary Pharmacology and Therapeutics 6 (2008) 33-40; Henry-Michelland e cols. Attachment of antibiotics to nanoparticles: preparation, drug release and antimicrobial activity in vitro". International Journal of Pharmaceutics 35 (1987) 121-127; Fattal E. e cols. "Ampicillin loaded liposomes and nanoparticles: comparison of drug loading, drug release and in vitro antimicrobial activity. Journal of Microencapsulation 8 (1991) 29-36; Anderson J C. e cols.". "The effect of incorporation of cloxacillin in liposomes on treatment of experimental staphylococcal mastitis in mice". Journal of veterinary pharmacology and therapeutics 9 (1986) 303-9 and in the documents of patent EP0260854 and WO9531180 (A1), the present invention deals with the encapsulation of antibiotics in nanocarriers with adhesive capacity in the udder of the animals.

In the research conducted in the literature and in the in patent databases, no registrations were found that related the antibiotic cloxacillin benzathine and nanocarriers with increased antibacterial effectiveness in the mastitis in the nanostructured form. Furthermore, in none of such documents it is made reference to the use of materials which enable the adhesion of the nanocarriers to the cells of the superior part of the teat after intramammary administration, which increases the chances of effectiveness of said new formulations for veterinary use in relation to the products sold and protected by patent. In the same context, there is no reference of polymeric nanoparticles containing cloxacillin benzathine with high possibility to penetrate the infected cells and release the drug in a prolonged form.

Patent WO9531180 describes a treatment for mastitis comprising an administration of a formulation composed by an aqueous suspension of cloxacillin benzathine micronized and subsequently of a gel containing heavy metal salts in order to seal the teat, which can cause a possible contamination of the milk through heavy metal salts in the period de lactating. Furthermore, in this document the results regarding the speed of release of the antibiotic are not disclosed.

Patent EP0260854 describes the microencapsulation of a mixture of cloxacillin benzathine and amplicilin trihydrate for the treatment of mastitis, but it exhibits a very large polydispersity of the particles, which make it difficult or impossible to predict the speed of release of the drug from such microstructures. However, the microcapsules have lower capacity of adhesion to the superior part of the teat cells due to its greater weight, which can lead to sedimentation close to the teat canal due to the difference in density, while the nanoparticulate form does not sediment due to its colloidal characteristics.

Patent RU2350332 describes an emulsion containing doxycycline for treatment of the mastitis in cow in the dry period, the disadvantage of being unstable in the physiological environment, mainly in the milk, which presents casein. Moreover, it does neither present controlled release, nor targeting of the drug. The emulsions are less stable biological environment due to the interactions with the lipoproteins, releasing the drug faster (Mosqueira et al., 2007). On the other hand, the nanocarriers have a polymer wall more resistant to degradation and that controls the drug release.

Patent CN101439044 describes a gel containing Polyvinylpyrrolidone (PVP-I) for treatment of mastitis, but presents the inconvenience of being able to cause an inflammatory reaction in the udder of the animal as adverse effect of the treatment, having the potential of producing a chemical mastitis induced by the irritating effect of iodine released.

Patents KR20080083499 and KR20070059787 use silver nanoparticles colloidal for treatment of mastitis, but have the disadvantage of the presence of residue in the milk or even the silver can cross the blood-glandular barrier reaching the systemic circulation.

The Cloxacillin in a sodic form is used for the treatment of mastitis during intramammary lactation. According to Anderson et al. (1986) the Cloxacillin encapsulated in liposomes was directed to the treatment of the mastitis in the stage of lactation, however, the use of release systems sustained during such period increases the discharge of milk, since the time of release of the drug is increased. The liposome has stability reduced in physiological environment when compared to the polymeric nanocarriers. Said treatment was performed in murine model, which is not directly related to the present proposal. The liposomes are formulated rather unstable, expensive and presenting difficult stabilization and production comparatively to the nanocapsules produced in this invention.

Modern carrier drug systems has been the target of numerous studies in the pharmaceutical area in order to control the speed of drug release in the organism, decreasing the dose required and increasing the selectivity in relation to the target (Schaffazick et al., 2003; Chacón et al., 1999; De Chasteigner et al., 1996; Santos-Magalhães et al., 2000).

The polymeric nanocarriers of the reservoir type consist of an oily core surrounded by a polymeric membrane (Legrand et al., 1999), working with the chosen carrier for the administration of the substances of low solubility in water as the cloxacillin benzathine, for they comprise stable polymers with low toxicity that comprise biocompatible and biodegradable material, which are degraded in vivo into smaller fragments easily excreted, as carbon dioxide and water.

For the preparation of the nanocarriers polymers generally in the range of 0.2 to 2% (p/p) are used. Polyesters, polyamides, polycyanoacrylates, polycarbonates, polyurethanes, chitosan, chitin, gelatine, methacrylates, copolymers of acrylic acid and acrylic esters, polyalkylacrylates, polymethacrylates, vinyl alcohol polymer, or combinations or mixtures of such material can be generally used. However the most suitable by its degradability are the polyesters hydroxyacids: Polyesters of lactic, glycolic acid and their co-polymers and their different combinations and proportions with molecular weight ranging from 2.000 to 1.00.000, namely: poly (D, L-lactic acid), poly (glycolic acid), poly (lactic-co-glycolic acid), poly-£-caprolactone, poly-β-hydroxybutyrate, β-poly (hydroxybutyrate-co-valerate) and poly (hydroxyalkanoates).

hydrophilic surfactants (such as polysorbates 20, 21, 40, 60, 61, 65, 80, 81, 85 and 120; copolymers of polyethylene oxide-polyethylene oxide propylene such as the poloxamers 124, 188, 237, 338 and 407) and lipophilic (sorbitan esters such as sorbitan monolaurate, sorbitan trilaurate, sorbitan monopalmitate, sorbitan monostearate, sorbitan tristearate, sorbitan monooleate, sorbitan trioleate; lecithins; polyglyceryl-6 (dioleate) are also usually used from 0.2 to-2% (w/w).

The oils used can be vegetable (soybean, corn, cottonseed, olive, almond, sunflower, grape) or mineral (liquid paraffin, liquid paraffin "light") or fatty acid esters (polyglyceryl-6 dioleate, polyethylene glycol-6 olive oil, peanuts and corn) and medium chain triglycerides (such as triglyceride of caprylic/capric acid), which should present no toxicity, not being able to degrade or solubilize the polymer and high capacity to dissolve the drug in question (Legrand et al., 1999).

The nanocarriers can have their surface modified by coating with chitosan. The nanocarriers herein proposed obtained from poly-£-caprolactone, for instance, concentrate the encapsulate drugs in cells of the mononuclear phagocyte system (MPS). The conventional nanocarriers coated with chitosan have a characteristic of biodiversity, which increases the particle retaining charged with drug in the action place, for instance, in the superior parts of the udder.

In this context, recent studies with nanocarriers of the reservoir type have been showing that such structures have specific advantages over liposomes, for they have a greater physical stability in biological environment, low inherent toxicity, high encapsulation of lipophilic substances in its oily core (Legrand et al., 1999, Mosqueira et al., 2001 and 2006). Besides that, they can be produced by simple, fast, efficient and of low costs methods. Similarly to the liposomes, the polymeric nanoparticles of the same size can also be captured by inflammatory foci due to increased of vascular permeability at determined place (Barratt, 2000), according to U.S. Pat. No. 6,171,796; U.S. Pat. No. 6,632,671 and U.S. Pat. No. 7,060,689 and PI0605102-2A.

The chitosan is a hydrophilic polysaccharide, amine derivative of the process of deacetylation of the chitin which forms the shell of insects and crustaceans. Being a natural and biodegradable polymer, chitosan has been proposed as an attractive material for various uses, especially in engineering, biotechnology and medicine (Hirano, 1999). Chitosan is insoluble in water, which can be characterized as a cationic polyelectrolyte. It is soluble in weak organic acids or diluted as 3% acetic acid producing a viscous solution. In order to solve the problem of the insolubility in water, which limits its application in vectors of drug, especially for vehicular peptides and genes, papers have been published bringing different methodologies for obtaining chitosan soluble in water (Signini and Campana, 2001; Garcia-Fuentes et al., 2005) since incubation until incorporation of chitosan to methods of producing pre-prepared nanoparticles. As an example, the coating of lipidic nanoparticles with negative surface charge have its charge inverted when the chitosan is incubated in the environment (Garcia Fuentes et al., 2005). Thus the resulting particles have surface properties and different stability from the originals. The adaptation of existing production methodologies to incorporate the chitosan can be evaluated based on the work from Calvo et al. (1997), where the addition of chitosan in the acidified aqueous phase permitted nanoemulsions and chitosan nanocapsules with chitosan adsorbed to the phospholipids of the wall according to patent U.S. Pat. No. 5,843,509. In the present invention the chitosan in salt form is used in neutral aqueous phase.

The cloxacillin is an β-lactam antibiotic used in veterinary practice due to of its activity against bacteria gram positive and negative, the drug is used in the treatment and prevention of mastitis bovina caused by *Staphylococcus* (Perez et al., 1997).

The advantage of this invention is in the creation of a new possibility of mastitis therapy in dairy cattle by intramammary in the dry period through the encapsulation of the drug cloxacillin benzathine in nanocarriers which are avidly phagocytosed by cells present in the infected parts of the interior of the mammary gland. Said nanocarriers have greater penetration in regions where the inflammation is present, as described in patent PI0605102-2A.

The formulations of nanocarriers of reservoir type used in this invention containing the cloxacillin benzathine in its interior were prepared with a method different from the one described by Fessi et al. (1989), regarding the constituents of the formulations and the proportions of the phases of the solvents, which were specific to the drug used.

The polymers used in the preparation of the nanocarriers herein proposed were the poly-£-caprolactone (PCL) and the chitosan (QUIT), both biocompatible and biodegradable, being easily excreted by the organism.

Thus, said nanostructures are interesting carriers due to their stability in biologic environment and low toxicity depending on the use of the biodegradable polymers. Considering all those aspects, the present invention was prepared to the use of veterinary medicine as a new way of treatment to the bovine mastitis through intramammary, in the dry period, having as principal advantages the ease handling in the moment of the use, the simplicity in the preparation and the viability to the sale. Besides this new possibility, said nanocarriers can also be used in the treatment of such and other diseases, provided that the affinity between the drug and the oily core.

The present invention is based in the fact that such nanostructured carriers are captured by the mononuclear phagocyte system and the ones of surface modified by the Chitosan are bioadhesive. Therefore, both formulations have potential of success in the treatment of the mastitis, due to the greater penetration into the affected tissue.

The nanocarriers of reservoir type were prepared by the method of interfacial deposition of preformed polymer followed by the displacement of miscible solvents with water and immiscible with oil and with the hydrophobic polymers.

Preliminary clinical studies indicate the improved effectiveness with the formulation proposed.

EXAMPLES

The experimental examples illustrate this invention, without however limit its application.

Example 1: Production of Nanocarriers of Reservoir Type Coated with Chitosan (NC PCL QUIT) Containing Antibiotic for Veterinary Use The nanocarriers of the cloxacillin benzathine were prepared according to the following constituents (% w/w):

| | |
|---|---|
| Poly-£-caprolactone | 0.80% |
| Soy lecithin | 0.40% |
| Labrafac CC | 0.25% |
| Poloxamer 188 | 0.60% |
| Chitosan | 0.10% |
| Cloxacillin benzathine | 0.25% |
| Water qsp | 100% |

For the preparation of the coated nanocarriers (NC-PCL-QUIT) containing cloxacillin benzathine, the polymer poly-£-caprolactone (PCL) was diluted in 23 ml of a solution of acetone containing soy lecithin (Epikuron 170) and Labrafac CC. The drug cloxacillin benzathine was previously solubilized in 7 ml of methanol and added to a solution of acetone. This phase remained for stirring and moderate heating (30 a 45° C.) until complete dissolution of the components. Subsequently, the organic solution was charged into an aqueous solution previously prepared containing poloxamer 188 and 10 mg of water-soluble chitosan, followed by stirring at moderate speed, the ambient temperature with the assistance of magnetic stirrer for ten minutes. After, such suspension was brought to the rotary evaporator, maintaining the bath temperature at 40-45° C. for evaporation of the solvents at reduced pressure. The size and the zeta potential of the nanocapsules obtained were 291 nm and +16 mV respectively. The efficiency of encapsulation was of 87%.

Example 2: Production of Conventional Nanocarriers (NC PCL) Containing Antibiotic of Veterinary Use The nanocarriers of cloxacillin benzathine were prepared according to the following constituents (% w/w):

| | |
|---|---|
| Poly-£-caprolactone | 6Ut |
| Sorbitan monooleate | 0.40% |

-continued

| | |
|---|---|
| Plurol oleique | 0.25% |
| Poloxamer 188 | 0.75% |
| Cloxacillin benzathine | 0.05% |
| Water qsp | 100% |

For the preparation of conventional nanocarriers containing cloxacillin benzathine, they were dissolute in 7 ml of a solution of acetone: The polymer poly-£-caprolactone (PCL), sorbitan monooleate and Plurol oleique. The drug cloxacillin benzathine was previously solubilized in 3 ml of methanol and added to a solution of acetone. Subsequently, the organic solution poured into an aqueous solution containing poloxamer 188. Followed by stirring with the assistance of magnetic stirrer for ten minutes. The evaporation of the solvents was carried out according to the abovementioned methodology. The size was determined by photon correlation spectroscopy and zeta potential by laser Doppler anemometry. The values were 322 nm and −28 mV respectively. The efficiency of encapsulation was of 37%. Through the atomic force microscopy (AFM), images of the nanocapsules were obtained, evidencing the character spherical and homogeneous of the particles.

TABLE 1

Analysis of the size and zeta potential of the nanocarriers containing different concentrations of cloxacillin benzathine.

| | % (p/v) PCL | % (p/v) QUIT | Contraction of CLOXB (mg/mL) | Average size ± $DP^1$ (nm) | Potential zeta$^3$ ± $DP^2$ (mV) |
|---|---|---|---|---|---|
| NC-PCL | 0.6 | — | 0 | 308.9 ± 8.2 | −30.47 ± 2.01 |
| NC-PCL | 0.6 | — | 0.5 | 322.4 ± 3.9 | −28.20 ± 0.62 |
| NC-PCL-QUIT | 0.8 | 0.1 | 0 | 214.3 ± 1.5 | +21.00 ± 0.53 |
| | 0.8 | 0.1 | 2.5 | 291 ± 5.6* | +16.53 ± |
| QUIT | 0.8 | 0.1 | 5 | 242.9 ± 5.7* | +14 ± 2.75* |

$^1$DP = Standard deviation (n = 3);
$^2$I.P = Index de polidispersao (n = 3);
$^3$Peak width equal to 1.6 in all samples. The statistical analysis was conducted through the t student test between the different formulations, in relation to the white NC. P < 0.05 for the parameters shown in the table in relation to the white formulation, except of the identified with *.

TABLE 2

Efficiency and yield of encapsulation of the NC containing different concentrations of cloxacillin benzathine.

| Nanocarriers | EE(%) | Yield |
|---|---|---|
| NO POL cloxacillin benzathine 0.5 mg/ml | 34% | 23% |
| NO POL cloxacillin benzathine 2.5 mg/ml | unstable | ND |
| NO POL-QUIT cloxacillin benzathine 2.5 mg/ml | 87% | 76% |
| NO POL-QUIT cloxacillin benzathine 5.0 mg/ml | unstable | ND |

ND—not determined

In case of nanostructures of PCL-QUIT, there is a presence of chitosan in the surface of such particles, a positively charged polymer that interacts with the anion cloxacillin, increasing its absorption in the surface.

Figure 1:
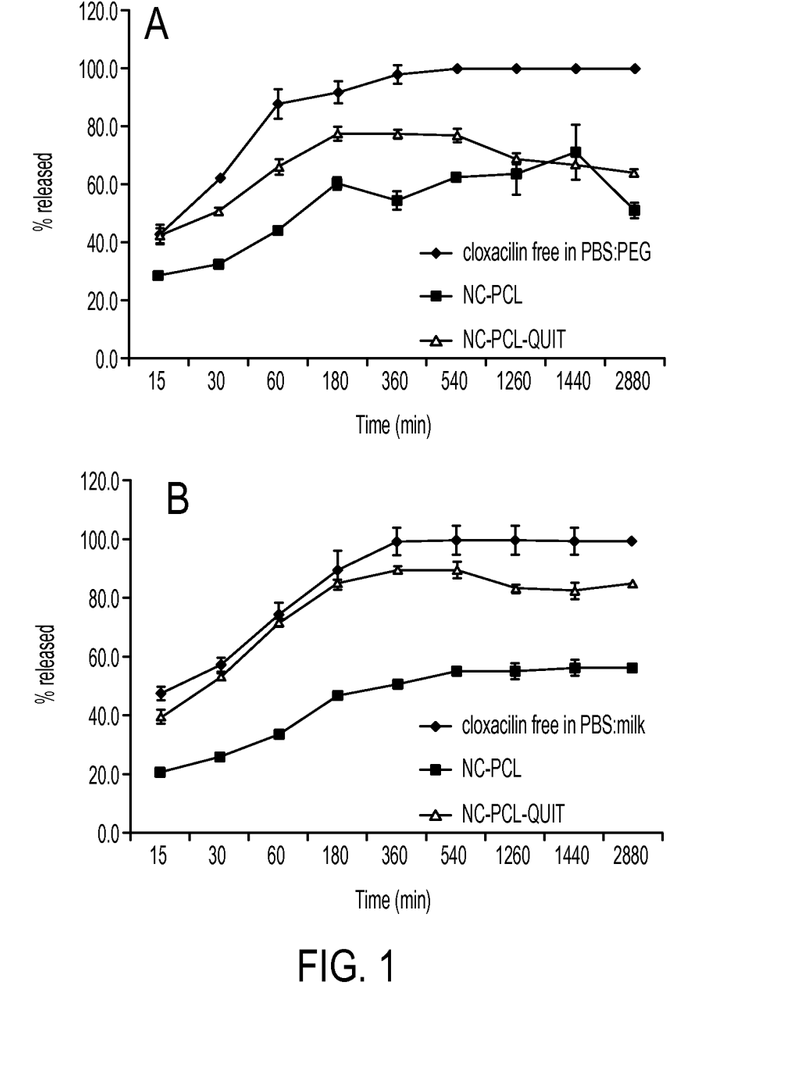
FIG. 1 shows the release profile of cloxacillin benzathine (CLOXB) in vitro under 37° C. in a buffered saline solution (PBS) environment containing 1% of polyethylene glycol and 1% of milk from the free cloxacillin and from the formulations of nanocarriers of poly-£-caprolactone (NC PCL) 0.5 mg and nanocarriers of a reservoir type coated with chitosan (NC PCL-QUIT) 2.5 mg in sink conditions.

FIG. 1 shows the release profile of the CLOXB in vitro under 37° C. in PBS environment containing 1% of polyethylene glycol and 1% of milk from the free cloxacillin and from the formulations of NC of PCL 0.5 mg and NC PLC-QUIT 2.5 mg in sink conditions.

The evaluation of the release profile in vitro of the cloxacillin benzathine from the nanocarriers of reservoir type was performed according to the direct dialysis technique in two different release environments. Dialysis bags were inserted in containers containing a buffered saline solution and 1% polyethylene glycol 300 (PBS:PEG) or a buffered saline containing 1% of skimmed milk (PBS:milk) under 37° C. with moderate stirring. In different dialysis bags with pores of 12.000 to 14.000 (cut off) were inserted: Free CLOXB, suspension of NC-PCL 0.5 mg/ml and suspension of NC-PCL-QUIT 2.5 mg/ml in the PBS:PEG and PBS: milk environments. In pre-defined lapses, aliquots were removed and the environment was re-added with the same volume withdrawn. Right after, the samples were prepared and the supernatant dosed.

According to FIG. 1, it is observed a slower release profile with the NC of 0.5 of CLOXB, since probably the quantity of the drug absorbed in the surface and ready for desorption is smaller than in the NC of 2.5 of CLOXB. The latter present a profile with plateau, probably due to the higher drug content adsorbed on the surface of NC containing chitosan. In the two formulations of NC the release presents an almost linear profile, which indicates controlled release in the first 6 h, followed by the appearance of a plateau, with retention of the remainder of CLOXB, probably related to the quantity located into the oily core of the NC. Irwin et al. (1984) it was observed that the CLOXB has its dissolution dependent on the pH value. Its group developed a study of dissolution of the CLOXB in environments with different pH values: 2, 6 and 9, where was observed that in pH 2 and 9 the cloxacillin degrades and, in pH 6 its dissolution is dependent of the solubility until 300 minutes of test. In this work, the dissolution was conducted in pH 7.4 for it is about the pH of the milk of animals with mastitis (Gruet et al., 2001). There was no degradation of the drug until 540 minutes of test by HPLC in such experimental conditions.

Regarding the drug release of the nanocapsules in different environments, it is observed that its profiles are different. The NC-PCL-QUIT 2.5 mg containing CLOXB showed a faster release, more than 70% in 6 h in an environment containing 1% of milk than in the environment containing 1% of PEG. On the other hand, the NC-PCL containing CLOXB showed a faster release in an environment with 1% of PEG than in an environment containing 1% of milk. Between the three graphics there are similarities in the release profile of the free CLOXB and of the encapsulated in NC-PCL. The release was bigger in environment containing 1% of PEG, differently of the NC-PCL-QUIT that have greater release in milk. Thus, nanocapsules containing the antibiotic cloxacillin benzathine are promising for the intramammary administration in dairy cattle.

As one can observe in FIG. 1, the retention of the cloxacillin benzathine in the nanocarriers is bigger with the polymer PCL (FIG. 1A). Even in environment containing milk (FIG. 1B) the drug retention and low speed of evidents compared to cloxacillin benzathine not charged. Said data attest the effectiveness of the formulation for slow release of CLOXB in the animal teat.

Figure 2:
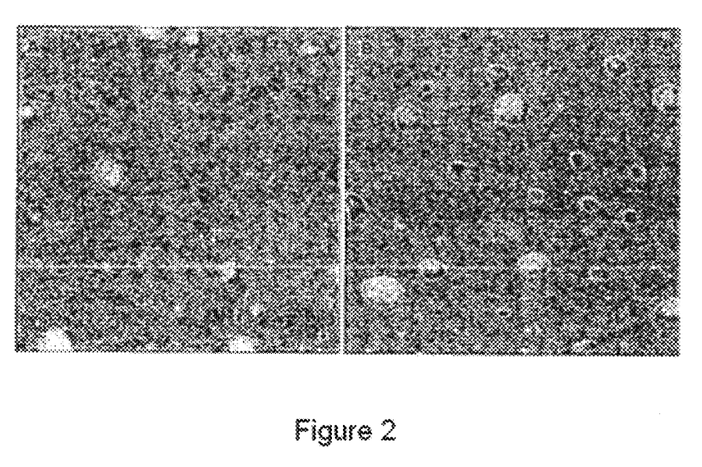
FIG. 2 shows images of atomic force microscopy (AFM) intermittently of nanocarriers of poly-£-caprolactone (NC-PCL) Image height, (A) White NC (B) NC PCL 0.5 mg/ml, scale: (5×5, µM).

FIG. 2 shows images of MFA intermittently de NC-PCL. Image height. (A) White NC (B) NC PCL 0.5 mg/ml. scale: (5×5, µM).

The invention claimed is:

1. A process for obtaining a nanoparticulate composition, comprising the steps of: preparing a fraction A that consists of a solution containing: (a) a hydrophobic polymer which is insoluble in water selected from the group consisting of polyesters of lactic, glycolic acids and co-polymers thereof; (b) oil; and (c) at least one lipophilic surfactant, all of which are dissolved in water-miscible organic solvents; preparing a fraction B containing at least an antimicrobial agent from the group of beta-lactams solubilized in an alcoholic solvent;

preparing a fraction C that consists of a mixture of the fractions A and B; preparing a fraction D that consists of a neutral aqueous solution containing a hydrophilic surfactant and a cationic polymer of the aminopolysaccharide type from the group of chitosans in the form of a water soluble salt; and simultaneously combining the fractions C and D with subsequent formation of nanoparticles coated with a polymer film.

2. A process for obtaining a nanoparticulate composition, comprising the steps of: preparing a fraction A that consists of a solution containing: (a) a hydrophobic polymer which is insoluble in water selected from the group consisting of poly-caprolactone (PCL), diblock and multiblock polymers derived from poly(lactic acid) polymers (PLA), poly(lactic-co-glycolic) acid (PLGA), polyglycolic acid (PGA), polyhydroxyalkanoates (PHA), poly-p-hydroxybutyrate and poly-3-(hydroxybutyrate-co-valerate); (b) oil; and (c) at least one lipophilic surfactant, all of which are dissolved in water-miscible organic solvents; preparing a fraction B containing at least an antimicrobial agent from the group of beta-lactams solubilized in an alcoholic solvent; preparing a fraction C that consists of a mixture of the fractions A and B; preparing a fraction D that consists of a neutral aqueous solution containing a hydrophilic surfactant and a cationic polymer of the aminopolysaccharide type from the group of chitosans in the form of a water soluble salt: and simultaneously combining the fractions C and D with subsequent formation of nanoparticles coated with a polymer film.

3. The process according to claim 1, wherein the amount of oil ranges between 0.25 to 5% w/v in relation to the final volume of the aqueous medium.

4. The process according to claim 1, wherein the antimicrobial agent is constituted by at least one substance selected from the following group: penicillin and derivatives thereof, benzathine penicillin, cloxacillin, dicloxacillin, flucloxacillin, cloxacillin benzathine, ampicillin, amoxicillin, hetacillin.

5. The process according to claim 1, wherein the amount of hydrophobic polymer ranges between 0.1 to 3% w/v in relation to the final volume of the aqueous medium.

6. The process according to claim 1, wherein the amount of cationic polymer ranges between 0.05 to 2% w/v in relation to the final volume of the aqueous medium.

7. The process according to claim 1, wherein the hydrophilic surfactant is selected from the group consisting of polysorbate 20 or 21 or 40 or 60 or 61 or 65 or 80 or 81 or 85 or 120; and derivatives of polyethylene oxide-propylene oxide co-polymer, wherein the amount added ranges between 0 to 2% w/v in relation to the final volume of the aqueous medium.

8. The process according to claim 1, wherein the lipophilic surfactant is selected from the group consisting of: derivatives of sorbitan esters and derivatives of lecithin, wherein the amount added ranges between 0.2 to 2% w/v in relation to the final volume of the aqueous medium.

9. The process according to claim 1, wherein the organic phase, consisting of the Fraction C, is mixed with a neutral aqueous phase, Fraction D, so that the total solvents are evaporated to less than one third of the total volume of the mixture at the end of the process.

10. The process according to claim 1, wherein the nanoparticulate composition is sterilized by passage through sterile filters of 0.2 to 0.8 µm diameter.

11. A nanoparticulate composition obtained through the process as described in claim 1.

12. A nanoparticulate composition consisting of an association of the composition obtained in accordance with claim 1, and a pharmaceutically acceptable vehicle.

13. A nanoparticulate composition consisting of an association of the composition obtained in accordance with claim 1 and one or more free active principles in solution, as well as, optionally, a pharmaceutically acceptable vehicle.

14. A method of treatment and prophylaxis of diseases in animals and/or pharmacologic support comprising administering an effective amount of the nanoparticulate composition obtained through the process described in claim 1, to an animal in need thereof or which may benefit therefrom.

15. A nanoparticle being constituted by a nanocarrier obtained through claim 1.

16. The process according to claim 7, wherein the derivatives of polyethylene oxide-propylene oxide co-polymer are poloxamer 124 or 188 or 237 or 338 or 407.

17. The process according to claim 8, wherein the derivatives of sorbitan esters are sorbitan monolaurate, sorbitan trilaurate, sorbitan monopalmitate, sorbitan monostearate, sorbitan tristearate, sorbitan monooleate, or sorbitan trioleate; and the derivatives of lecithin are soy lecithin.

18. The process according to claim 2, wherein the antimicrobial agent is constituted by at least one substance selected from the following group: penicillin and derivatives thereof, benzathine penicillin, cloxacillin, dicloxacillin, flucloxacillin, cloxacillin benzathine, ampicillin, and hetacillin.

19. The process according to claim 1, wherein nanoparticles obtained by the process have a positive surface charge that ranges between +10 and +30 mV.

\* \* \* \* \*